United States Patent [19]

Böhner et al.

[11] 4,054,575

[45] Oct. 18, 1977

[54] 1,2,4-TRIAZOLYL-PHOSPHORIC ACID AND PHOSPHONIC ACID ESTERS

[75] Inventors: Beat Böhner, Binningen; Dag Dawes, Pratteln; Willy Meyer, Basel, all of Switzerland

[73] Assignee: Ciba-Geigy Corporation, Ardsley, N.Y.

[21] Appl. No.: 422,037

[22] Filed: Dec. 5, 1973

[30] Foreign Application Priority Data

Dec. 8, 1972 Switzerland .................. 17894/72
Nov. 2, 1973 Switzerland .................. 15457/73

[51] Int. Cl.² .................. A01N 9/36; C07F 9/65
[52] U.S. Cl. .................. 260/308 R; 424/170; 424/200
[58] Field of Search .................. 260/308 R

[56] References Cited

U.S. PATENT DOCUMENTS 3,867,397   2/1975   Bohner et al. .................. 260/308 R
3,867,398   2/1975   Bohner et al. .................. 260/308 R Primary Examiner—Alton D. Rollins
Attorney, Agent, or Firm—Frederick H. Rabin

[57] ABSTRACT

1,2,4-triazolylphosphoric and 1,2,4-triazolylphosphonic acid esters of the formula

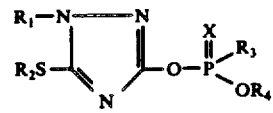

wherein $R_1$ represents hydrogen, alkyl, cycloalkyl, phenyl, benzyl, or phenethyl, $R_2$ represents alkenyl or alkinyl, $R_3$ represents alkyl, alkoxy, alkylthio, amino, monoalkylamino or dialkylamino, $R_4$ represents alkyl, and X represents oxygen or sulphur, a process for their manufacture and their use in pest control.

11 Claims, No Drawings

1,2,4-TRIAZOLYL-PHOSPHORIC ACID AND PHOSPHONIC ACID ESTERS

The present invention relates to 1,2,4-triazolylphosphoric and 1,2,4-triazolylphosphonic acid esters, to a process for their manufacture, and to their use in pest control. The 1,2,4-triazolylphosphoric and 1,2,4-triazolylphosphonic acid esters have the formula

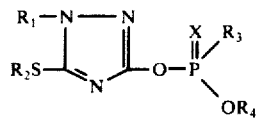
(I)

wherein $R_1$ represents hydrogen, alkyl, cycloalkyl, phenyl, benzyl, or phenethyl, $R_2$ represents alkenyl or alkinyl, $R_3$ represents alkyl, alkoxy, alkylthio, amino, monoalkylamino or dialkylamino, $R_4$ represents alkyl, and X represents oxygen or sulphur.

By an alkyl, alkoxy, alkylthio, a monoalkylamino, dialkylamino, an alkenyl or alkinyl radical is meant in each case a straight-chain or branched unsubstituted radical with 1 to 12 carbon atoms, the alkinyl and alkenyl radicals containing from 2 to 12, preferably from 1 to 6 and 3 to 5, carbon atoms respectively.

Examples of such radicals include: methyl, methoxy, methylthio, ethyl, ethoxy, ethylthio, propyl, propoxy, propylthio, isopropyl, isopropoxy, isopropylthio, n-butyl, iso-butyl, sec. and tert. butyl, n-pentyl, n-hexyl and isomers thereof, n-penthylthio, methylamino, dimethylamino, allyl, methallyl, propargyl.

The cycloalkyl radicals possible for $R_1$ have 3 to 8, in particular 3 to 6, ring carbon atoms. Preferred cycloalkyl radicals are cyclopropyl, cyclopentyl or cyclohexyl.

The phenyl, benzyl and phenethyl groups represented by $R_1$ can be unsubstituted at the rings or substituted e.g. by methoxy, halogen atoms, such as fluorine, chlorine, bromine and/or iodine, preferably chlorine, nitro, alkyl with 1 to 5 carbon atoms and/or haloalkyl with 1 to 5 carbon atoms.

Important compounds on account of their action are those of the formula I wherein $R_1$ represents hydrogen, alkyl with 1 to 6 carbon atoms, cycloalkyl with 3 to 6 carbon atoms, unsubstituted phenyl or phenyl which is monoor polysubstituted, in like manner or differently, by fluorine, chlorine, bromine, trifluoromethyl, nitro, or methyl, $R_2$ represents alkenyl or alkinyl, each with 3 to 5 carbon atoms, which is mono- or disubstituted by chlorine, $R_3$ represents alkyl with 1 to 6 carbon atoms, alkoxy with 1 to 6 carbon atoms, alkylthio with 1 to 6 carbon atoms, amino, alkylamino with 1 to 6 carbon atoms, or dialkylamino with 2 to 6 carbon atoms, $R_4$ represents alkyl with 1 to 6 carbon atoms, and X represents oxygen or sulphur.

Preferred compounds are those of the formula I wherein $R_1$ represents alkyl with 1 to 6 carbon atoms or cycloalkyl with 3 to 6 carbon atoms, $R_2$ represents allyl, methallyl, 2-butenyl, 4-chloro-2-butenyl or propargyl, $R_3$ represents methoxy, ethoxy, or ethylamino, $R_4$ represents methyl or ethyl, and X represents sulphur.

Particularly preferred compounds, however, are those of the formula I wherein $R_1$ represents methyl, ethyl, isopropyl, or cyclopentyl, $R_2$ represents allyl, methallyl, 2- butenyl, 4-chloro-2-butenyl, or propargyl, $R_3$ represents ethoxy or methylamino, $R_4$ represents ethyl, and X represents sulphur.

The compounds of the formula I can be manufactured by methods which are known per se by a. reacting a hydroxy-triazole of the formula

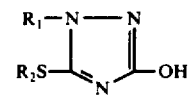
(II)

in the presence of an acid acceptor, with a compound of the formula

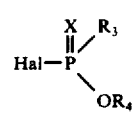
(III)

or b. reacting a hydroxy-triazole of the formula

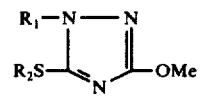
(IV)

with a compound of the formula

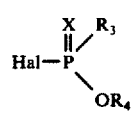
(III)

or c. reacting a hydroxy-triazole of the formula

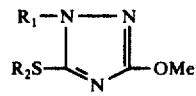
(IV)

with a compound of the formula

$R_4-O-PX-Cl_2$ (V)

and reacting the intermediate product of the formula

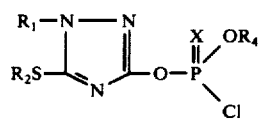
(VI)

subsequently with a compound of the formula $HN(Alkyl)_2$ (VII)

(VIII)

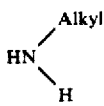

(IX)

wherein $R_1$ to $R_4$ and X have the meanings given for the formula I, Hal represents a halogen atom, especially chlorine or bromine, and Me represents a monovalent metal, in particular an alkali metal.

Examples of suitable acid acceptors are: tertiary amines, such as triethylamine, dimethyl aniline, pyridine, inorganic bases, such as hydroxides and carbonates of alkali metals and alkaline earth metals, preferably sodium and potassium carbonate.

The reactions can take place preferably in solvents or diluents which are inert towards the reactants. Suitable examples of such solvents or diluents are: aromatic hydrocarbons, e.g. benzene, toluene, halogenated hydrocarbons, chlorobenzene, polychlorobenzenes, bromobenzene, chlorinated alkanes with 1 to 3 carbon atoms, ethers, e.g. dioxan, tetrahydrofuran, esters, e.g. ethyl acetate, ketones, e.g. acetone, methyl ethyl ketone, diethyl ketone, nitriles, e.g. acetonitrile etc.

Starting materials of the formulae II and IV are new and can be synthesised in analogous manner to the method described in Belgian Pat. No. 792,449. It is also possible to manufacture the starting materials by reacting a 5-halo- 3-hydroxy-1,2,4-triazole derivative with metal salts of corresponding mercaptans.

The compounds of the formula I have a broad biocidal activity and can be used for combating a variety of plant and animal pests.

In particular they are suitable for combating insects of the families:

Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Paralidae, Galleriidae, Culicidae, Tipulidae, Stomoxydae, Muscidae, Calliphoridae, Trypetidae, Pulicidae, as well as Acaridae of the families: Ixodidae, Argasidae, Tetranychidae, Dermanyssidae.

By addition of other insecticides and/or acaricides it is possible to improve substantially the insecticidal or acaricidal action and do adapt it to given circumstances.

Examples of suitable additives are: organic phosphorus compounds, nitrophenols and derivatives thereof; pyrethrines; formamidines; ureas; carbamates and chlorinated hydrocarbons.

In addition to the above mentioned properties, the compounds of the formula I also exhibit a microbiocidal action. Thus a number of these compounds display bactericidal action. But they are active chiefly against fungi, especially against phytopathogenic fungi belonging to the following classes: Oomycetes, Zygomycetes, Ascomycetes, Basidiomycetes, Denteromycetes.

The compounds of the formula I also exhibit a fungitoxic action against fungi which attack the plants from the soil. The new active substances are also suitable for treating seeds, fruit, tubers, etc. from attack by fungus infections. The compounds of the formula I are also suitable for comparing phytopathogenic nematodes.

The compounds of the formula I may be used as pure active substance or together with suitable carriers and-/or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms:

Solid forms:
dusts, tracking agents, granules, coated granules, impregnated granules and homogeneous granules.

Liquid forms:
a. active substances which are dispersible in water: wettable powders, pasts, emulsions:
b. solutions.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows

Dusts

The following substances are used to manufacture (a) a 5% and (b) a 2% dust:
a. 5 parts of active substance
  95 parts of talcum
b. 2 parts of active substance
  1 part of highly disperse silicic acid
  97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3–0.8 mm).

The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

Wettable powder

The following constituents are used for the preparation of (a) a 40%, (b) and (c) a 25%, and (d) a 10% wettable powder:
a. 40 parts of active substance,
  5 parts of sodium lignin sulphonate, 1 part of sodium dibutyl-naphthalene sulphonate,
54 parts of silicic acid.

b. 25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin.

c. 25 parts of active substance,
  2.5 parts of isooctylphenoxy-polyoxyethylene-ethanol,
  1.7 parts of champagne chalk/hydroxyethyl cellulose mixture (1:1),
  8.3 parts of sodium aluminium silicate,
  16.6 parts of kieselguhr,
  46 parts of kaolin.

d. 10 parts of active substance,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a. 10 parts of active substance,
  3.4 parts of epoxidised vegetable oil,
  13.4 parts of a combination emulsifier consisting of fatty alcohol polyglycol ether and alkylaryl sulphonate calcium salt,
  40 parts of dimethylformamide,
  43.2 parts of xylene,
  25 parts of active substance,
  2.5 parts of epoxidised vegetable oil,
  10 parts of an alkylarylsulphonate/fatty alcoholglycol ether mixture,
  5 parts of dimethylformamide,
  57.5 parts of xylene.

From these concentrates it is possible to produce, by dilution with water, emulsions of any desired concentration.

Spray

The following constituents are used to prepared a 5% spray:
  5 parts of active substance,
  1 part of epichlorohydrin,
  94 parts of benzene (boiling limits 160° C–190° C).

EXAMPLE 1

A. Manufacture of the starting materials
1-methyl-3-hydroxy-5-propargylmercapto-1,2,4-triazole 13.1 g of 1-methyl-3-hydroxy-5-mercapto-1,2,4-triazole and 13.1 g of propargyl bromide are added to 100 ml of ethanol. To this suspension are added all at once 11.1 g of triethylamine. The exothermic reaction causes the temperature to rise to 45° C. After a short time a yellow product falls out of the clear solution and is filtered off and washed with water. The undissolved material is dried over $P_2O_5$.

| Analysis: | found: | calculated: | m.p. |
|---|---|---|---|
| | C 42.6 % | 42.59 % | 174–175° C |
| | H 4.3 % | 4.17 % | |
| | N 24.6 % | 24.83 % | |
| | S 19.5 % | 18.95 % | |

1-methyl-3-hydroxy-15-(β-methallyl)mercapto-1,2,4-triazole 11.1 g of triethylamine are added at room temperature to a suspension of 13.1 g of 1-methyl-3-hydroxy-5-mercapto-1,2,4-triazole in 100 ml of ethanol. The exothermic reaction causes the temperature to rise to 45° C. 10.0 g of β-methallyl chloride are added to the reaction mixture. The solution, which is now clear, is stirred for 15 minutes and evaporated. The solid residue is treated with about 50 ml of water and undissolved material is filtered off. This material can be recrystallised from acetonitrile.

| Analysis: | found: | calculated: | m.p. |
|---|---|---|---|
| | C 45.5 % | 45.39 % | 101–103° C |
| | H 6.0 % | 5.99 % | |
| | N 22.6 % | 22.68 % | |

The following compounds are also manufactured in analogous manner:

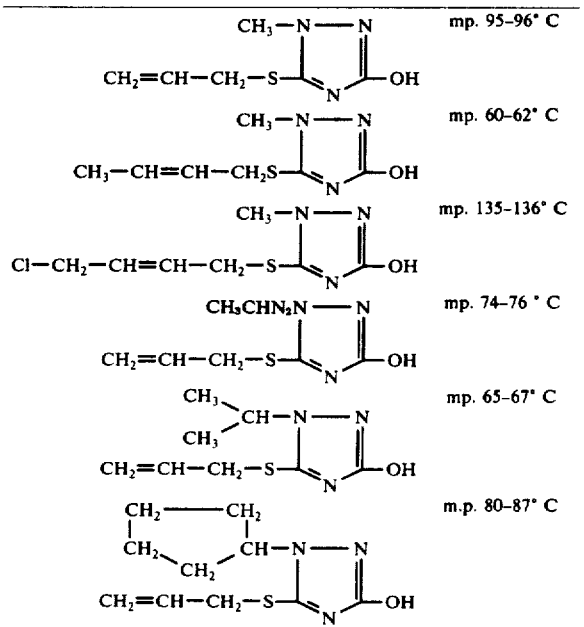

B. Manufacture of the active substances

O,O-diethyl-O-(1-methyl-5-propargylthio-1,2,4-triazolyl-(3)-thiophosphoric acid ester 16.9 g of 1-methyl-5-propargylthio-3-hydroxy-1,2,4-triazole and 13.8 g of potassium carbonate are refluxed for 2 hours in 300 ml of methyl ethyl ketone. The mixture is cooled to 40° C and then 19 g of diethylthiophosphoric chloride are added dropwise within 10 minutes. The mixture is again refluxed for 2 hours. After the mixture has cooled to room temperature, the insoluble salts are filtered off and the filtrate is concentrated in vacuo. The residual oil is purified by chromatography over a silica gel column with chloroform as eluant. The solvent is distilled off to give a light yellow oil of the formula

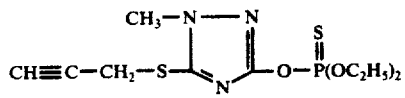

with a refractive index of $n_D^{20} = 1.5232$.

The following compounds were also manufactured in analogous manner:

| $R_1$ | $R_2$ | X | $R_3$ | $R_4$ | Physical data |
|---|---|---|---|---|---|
| $CH_3$ | $CH_2=CH-CH_2-$ | S | $OC_2H_5$ | $C_2H_5$ | $n_D^{20} = 1.5209$ |
| $CH_3$ | $CH_2=C(CH_3)-CH_2-$ | S | $NH-CH_3$ | $C_2H_5$ | $n_D^{20} = 1.5400$ |
| $CH_3-$ | $CH_3CH=CH-CH_2-$ | S | $OC_2H_5$ | $C_2H_5$ | $n_D^{20} = 1.5200$ |
| $CH_3$ | $Cl-CH_2-CH=CH-CH_2-$ | S | $OC_2H_5$ | $C_2H_5$ | $n_D^{20} = 1.5232$ |
| $CH_3$ | $CH_2=CH-CH_2-$ | S | $OCH_3$ | $CH_3$ | $n_D^{20} = 1.5321$ |
| $C_2H_5$ | $CH_2=CH-CH_2-$ | S | $OC_2H_5$ | $C_2H_5$ | $n_D^{20} = 1.5125$ |
| $(i)C_3H_7$ | $CH_2=CH-CH_2-$ | S | $OC_2H_5$ | $C_2H_5$ | $n_D^{20} = 1.5103$ |
| cyclopentyl | $Cl-CH=C(Cl)-CH_2-$ | S | $OC_2H_5$ | $C_2H_5$ | $n_D^{20} = 1.5256$ |

It is also possible to manufacture the following compounds in analogous manner:

| $R_1$ | $R_2$ | X | $R_3$ | $R_4$ | Physical data |
|---|---|---|---|---|---|
| $CH_3$ | $CH_2=CH-CH_2-$ | S | $SC_3H_7$ | $C_2H_5$ | |
| $CH_3$ | $CH_2=CH-CH_2-$ | S | $C_2H_5$ | $C_2H_5$ | |
| $CH_3$ | $CH_2=CH-CH_2-$ | S | $NH-C_3H_7(n)$ | $C_2H_5$ | |
| $CH_3$ | $CH_2=CH-CH_2-$ | S | $OC_2H_5$ | $C_2H_5$ | |
| $CH_3$ | $CH_2=C(CH_3)-CH_2-$ | S | $OCH_3$ | $CH_3$ | |
| $CH_3$ | $CH_2=C(CH_3)-CH_2-$ | S | $SC_3H_7$ | $C_2H_5$ | |
| $CH_3$ | $CH_2=C(CH_3)-CH_2-$ | S | $C_2H_5$ | $C_2H_5$ | |
| $CH_3$ | $CH_2=C(CH_3)-CH_2-$ | S | $CH_3$ | $C_2H_5$ | |
| $CH_3$ | $CH_2=C(CH_3)-CH_2-$ | S | $CH_3$ | $C_3H_7$ | |
| $CH_3$ | $CH_2=C(CH_3)-CH_2-$ | S | $NH-C_3H_7(i)$ | $C_2H_5$ | |
| $CH_3$ | $CH_2=C(CH_3)-CH_2-$ | O | $OC_2H_5$ | $C_2H_5$ | |
| $CH_3$ | $CH_3-CH=CH-CH_2-$ | S | $OC_2H_5$ | $C_2H_5$ | |
| $CH_3$ | $CH_3-CH=CH-CH_2-$ | S | $OCH_3$ | $CH_3$ | |
| $CH_3$ | $CH_3-CH=CH-CH_2-$ | S | $C_2H_5$ | $C_2H_5$ | |
| $CH_3$ | $HC≡C-CH_2-$ | S | $OC_2H_5$ | $C_2H_5$ | |

-continued

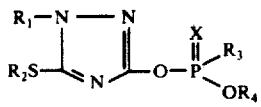

| $R_1$ | $R_2$ | X | $R_3$ | $R_4$ | Physical data |
|---|---|---|---|---|---|
| $CH_3$ | $HC\equiv C-CH_2-$ | S | $OCH_3$ | $CH_3$ | |
| $CH_3$ | $HC\equiv C-CH_2-$ | S | $SC_3H_7$ | $C_2H_5$ | |
| $CH_3$ | $HC\equiv C-CH_2-$ | S | $C_2H_5$ | $C_2H_5$ | |
| $CH_3$ | $HC\equiv C-CH_2-$ | S | $NH-CH_3$ | $CH_3$ | |
| $CH_3$ | $HC\equiv C-CH_2-$ | S | $NH-C_3H_7(n)$ | $C_2H_5$ | |
| $CH_3$ | $HC\equiv C-CH_2-$ | S | $NH-C_3H_7(i)$ | $C_2H_5$ | |
| $CH_3$ | $HC\equiv C-CH_2-$ | O | $OC_2H_5$ | $C_2H_5$ | |
| $CH_3$ | $HC\equiv C-CH(CH_3)-$ | S | $OC_2H_5$ | $C_2H_5$ | |
| $CH_3$ | $HC\equiv C-CH(CH_3)-$ | S | $OCH_3$ | $CH_3$ | |
| $CH_3$ | $HC\equiv C-CH(CH_3)-$ | S | $SC_3H_7$ | $C_2H_5$ | |
| $CH_3$ | $HC\equiv C-CH(CH_3)-$ | S | $C_2H_5$ | $C_2H_5$ | |
| $CH_3$ | $HC\equiv C-CH(CH_3)-$ | S | $NH-CH_3$ | $C_2H_5$ | |
| $CH_3$ | $HC\equiv C-CH(CH_3)-$ | S | $N(CH_3)_2$ | $C_2H_5$ | |
| $CH_3$ | $HC\equiv C-C(CH_3)_2-$ | S | $OC_2H_5$ | $C_2H_5$ | |
| $CH_3$ | $HC\equiv C-C(CH_3)_2-$ | S | $OCH_3$ | $CH_3$ | |
| $CH_3$ | $Cl-CH_2-CH=CH-CH_2-$ | S | $OC_2H_5$ | $C_2H_5$ | |
| $CH_3$ | $Cl-CH_2-CH=CH-CH_2-$ | S | $OCH_3$ | $CH_3$ | |
| $CH_3$ | $Cl-CH_2-CH=CH-CH_2-$ | S | $C_2H_5$ | $C_2H_5$ | |
| $CH_3$ | $Cl-CH_2-CH=CH-CH_2-$ | S | $SC_3H_7$ | $OC_2H_5$ | |
| $CH_3$ | $Cl-CH=CH-CH_2-$ | S | $OC_2H_5$ | $C_2H_5$ | |
| $CH_3$ | $Cl-CH=CH-CH_2-$ | S | $OCH_3$ | $CH_3$ | |
| $CH_3$ | $Cl-CH=CH-CH_2-$ | S | $NH-C_3H_7(n)$ | $C_2H_5$ | |
| $CH_3$ | $CH_2=C(Cl)-CH_2-$ | S | $OC_2H_5$ | $C_2H_5$ | |
| $CH_3$ | $CH_2=C(Cl)-CH_2-$ | S | $OCH_3$ | $CH_3$ | |
| $CH_3$ | $CH_2=C(Cl)-CH_2-$ | S | $NH-CH_3$ | $C_2H_5$ | |
| $CH_3$ | $CH_2=C(Cl)-CH_2-$ | S | $C_2H_5$ | $C_2H_5$ | |
| $CH_3$ | $Cl-CH=C(Cl)-CH_2-$ | S | $OC_2H_5$ | $C_2H_5$ | |
| $C_2H_5$ | $CH_2=C(CH_3)-CH_2-$ | S | $OC_2H_5$ | $C_2H_5$ | |
| $C_2H_5$ | $HC\equiv C-CH_2-$ | S | $OC_2H_5$ | $C_2H_5$ | |
| $C_2H_5$ | $HC\equiv C-CH(CH_3)-$ | S | $OC_2H_5$ | $C_2H_5$ | |
| $C_2H_5$ | $Cl-CH_2-CH=CH-CH_2-$ | S | $OC_2H_5$ | $C_2H_5$ | |
| $C_2H_5$ | $CH_2=C(Cl)-CH_2-$ | S | $OC_2H_5$ | $C_2H_5$ | |

-continued $$R_1-N-N$$
$$R_2S-\underset{N}{\overset{}{\bigvee}}-O-\overset{X}{\underset{OR_4}{P}}\overset{R_3}{}$$

| R₁ | R₂ | X | R₃ | R₄ | Physical data |
|---|---|---|---|---|---|
| (n)C₃H₇ | CH₂=C(CH₃)−CH₂− | S | OC₂H₅ | C₂H₅ | |
| (n)C₃H₇ | HC≡C−CH₂− | S | OC₂H₅ | C₂H₅ | |
| (i)C₃H₇ | HC≡C−CH₂− | S | OC₂H₅ | C₂H₅ | |
| (i)C₃H₇ | HC≡C−CH(CH₃)− | S | OC₂H₅ | C₂H₅ | |
| (i)C₃H₇ | Cl−CH=CH−CH₂− | S | OC₂H₅ | C₂H₅ | |
| (i)C₃H₇ | CH₂=C(Cl)−CH₂− | S | OC₂H₅ | C₂H₅ | |
| (i)C₃H₇ | Cl−CH=C(Cl)−CH₂− | S | OC₂H₅ | C₂H₅ | |
| cyclopentyl | CH₂=C(CH₃)−CH₂− | S | OC₂H₅ | C₂H₅ | |
| cyclopentyl | HC≡C−CH₂− | S | OC₂H₅ | C₂H₅ | |
| cyclopentyl | HC≡C−CH(CH₃)− | S | OC₂H₅ | C₂H₅ | |
| phenyl | CH₂=CH−CH₂− | S | OC₂H₅ | C₂H₅ | |
| phenyl | CH₂=CH−CH₂− | S | OCH₃ | CH₃ | |
| phenyl | CH₂=CH−CH₂− | S | NH−C₂H₅ | C₂H₅ | |
| phenyl | CH₂=CH−CH₂− | S | NH−CH₃ | C₂H₅ | |
| phenyl | CH₂=CH−CH₂− | S | NH−C₃H₇(n) | C₂H₅ | |
| phenyl | CH₂=C(CH₃)−CH₂− | S | OC₂H₅ | C₂H₅ | |
| phenyl | CH₂=C(CH₃)−CH₂− | S | OCH₃ | CH₃ | |
| phenyl | CH₂=C(CH₃)−CH₂− | S | C₂H₅ | C₂H₅ | |
| phenyl | CH₂=C(CH₃)−CH₂− | S | NH−CH₃ | CH₃ | |
| phenyl | CH₂=C(CH₃)−CH₂− | S | NH−C₃H₇(i) | C₂H₅ | |
| phenyl | CH₃−CH=CH−CH₂− | S | OC₂H₅ | C₂H₅ | |
| phenyl | HC≡C−CH₂ | S | OC₂H₅ | C₂H₅ | |
| phenyl | HC≡C−CH₂− | S | OCH₃ | CH₃ | |
| phenyl | HC≡C−CH₂− | S | C₂H₅ | C₂H₅ | |
| phenyl | HC≡C−CH₂− | S | CH₃ | C₃H₇(n) | |
| phenyl | HC≡C−CH₂− | S | NH₂ | C₂H₅ | |

-continued $$\begin{array}{c} R_1-N-N \\ R_2S-\underset{N}{\overset{\|}{C}}-O-\overset{X}{\underset{OR_4}{P}}\overset{R_3}{\diagdown} \end{array}$$

| R₁ | R₂ | X | R₃ | R₄ | Physical data |
|---|---|---|---|---|---|
| C₆H₅ | HC≡C—CH₂— | S | NH—CH₃ | C₂H₅ | |
| C₆H₅ | HC≡C—CH₂— | S | NH—C₃H₇(n) | C₂H₅ | |
| C₆H₅ | HC≡C—CH₂— | S | SC₃H₇(n) | C₂H₅ | |
| C₆H₅ | HC≡C—CH₂— | O | SC₃H₇(n) | C₂H₅ | |
| C₆H₅ | HC≡C—CH(CH₃)— | S | OC₂H₅ | C₂H₅ | |
| C₆H₅ | HC≡C—CH(CH₃)— | S | OCH₃ | CH₃ | |
| C₆H₅ | HC≡C—CH(CH₃)— | S | NH—CH₃ | C₂H₅ | |
| C₆H₅ | HC≡C—CH(CH₃)— | S | C₂H₅ | C₂H₅ | |
| C₆H₅ | HC≡C—C(CH₃)₂— | S | OC₂H₅ | C₂H₅ | |
| C₆H₅ | HC≡C—C(CH₃)₂— | S | OCH₃ | CH₃ | |
| C₆H₅ | Cl—CH₂—CH=CH—CH₂— | S | OC₂H₅ | C₂H₅ | |
| 3-Cl—C₆H₄— | HC≡C—CH₂— | S | OC₂H₅ | C₂H₅ | |
| 3-F₃C—C₆H₄— | HC≡C—CH₂— | S | OC₂H₅ | C₂H₅ | |
| 4-Br—C₆H₄— | HC≡C—CH₂— | S | OC₂H₅ | C₂H₅ | |
| 4-F—C₆H₄— | HC≡C—CH₂— | S | OC₂H₅ | C₂H₅ | |
| 3-Cl-5-CH₃—C₆H₃— | HC≡C—CH₂— | S | OC₂H₅ | C₂H₅ | |
| 4-O₂N—C₆H₄— | HC≡C—CH₂— | S | OC₂H₅ | C₂H₅ | |
| H | CH₂=CH—CH₂— | S | OC₂H₅ | C₂H₅ | |
| H | CH₂=CH—CH₂— | S | OCH₃ | CH₃ | |
| H | CH₂=CH—CH₂— | S | C₂H₅ | C₂H₅ | |
| H | CH₂=C(CH₃)—CH₂— | S | OC₂H₅ | C₂H₅ | |
| H | CH₂=C(CH₃)—CH₂— | S | OCH₃ | CH₃ | |
| H | CH₂=C(CH₃)—CH₂— | S | CH₃ | C₃H₇(n) | |
| H | CH₂=C(CH₃)—CH₂— | S | NH—C₃H₇(i) | C₂H₅ | |

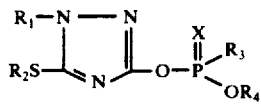

-continued

| $R_1$ | $R_2$ | X | $R_3$ | $R_4$ | Physical data |
|---|---|---|---|---|---|
| H | $HC\equiv C-CH_2-$ | S | $OC_2H_5$ | $C_2H_5$ | |
| H | $HC\equiv C-CH_2-$ | S | $OCH_3$ | $CH_3$ | |
| H | $HC\equiv C-CH_2-$ | S | $CH_3$ | $C_2H_5$ | |
| H | $HC\equiv C-CH_2-$ | S | $NH-C_3H_7(n)$ | $C_2H_5$ | |
| H | $HC\equiv C-CH-$<br>$\quad\quad\quad\vert$<br>$\quad\quad\quad CH_3$ | S | $OC_2H_5$ | $C_2H_5$ | |
| H | $\quad\quad\quad CH_3$<br>$\quad\quad\quad\vert$<br>$HC\equiv C-C-$<br>$\quad\quad\quad\vert$<br>$\quad\quad\quad CH_3$ | S | $OC_2H_5$ | $C_2H_5$ | |
| H | $Cl-CH=CH-CH_2-$ | S | $OC_2H_5$ | $C_2H_5$ | |
| H | $CH_2=C-CH_2-$<br>$\quad\quad\vert$<br>$\quad\quad Cl$ | S | $OC_2H_5$ | $C_2H_5$ | |

EXAMPLE 2

A. Insecticidal ingest poison action

Cotton and potato plants were sprayed with a 0.05% aqueous emulsion (obtained from a 10% emulsifiable concentrate). After the coating had dried, the cotton plants were populated with *Spodoptera littoralis* or *Heliothis virescens* larvae L₃ and the potato plants with Colorado potato bettle larvae (*Leptinotarsa decemlineata*). The test was carried out at 24° C and 60% relative humidity. In the above test, the compounds according to Example 1 displayed good ingest poison action against *Spodoptera littoralis*. Heliothis and *Leptinotarsa decemlineata* larvae.

B. System insecticidal action

To determine the systemic action, rooted bean plants (Vicia fabae) were put into a 0.01% aqueous active substance solution (obtained from a 10% emulsifiable concentrate). After 24 hours, aphide (*Aphis fabae*) were placed on the parts of the plant above the soil. The aphids were protected from contact and gas action by means of a special device. The test was carried out at 24° C and 70° C relative humidity. In the above test, the compounds according to Example 1 have systemic action against *Aphis fabae*.

EXAMPLE 3

Action against *Chilo suppressalis*

Six rice plants at a time of the variety Caloro were transplanted into plastic pots (diameter at the top = 17 cm) and reared to a height of about 60 cm. Infestation with *Chilo suppressalis* larvae (L₁: 3-4 mm long) took place 2 days after the active substance had been applied in granule form to the paddy water (rate of application: 8 kg of active substance per hectare). Evaluation of the insecticidal action took place 10 days after application of the granules. The compounds according to Example 1 were active in the above test against *Chilo suppressalis*.

EXAMPLE 4

Action against ticks

A. *Rhipicephalus bursa*

Five adult ticks and 50 tick larvae were counted into a glass tube and immersed for 1 to 2 minutes in 2 ml of an aqueous emulsion from an emulsion series each containing 100, 10, 1 or 0.1 ppm of test substance. The tube was then sealed with a standardised cotton wool plug and placed on its head, so that the active substance emulsion could be absorbed by the cotton wool.

In the case of the adults evaluation took place after 2 weeks, and in that of the larvae after 2 days. Each test was repeated twice.

B. *Boophilus microplus* (larvae)

Tests were carried out in each case with 20OP-sensitive larvae using a dilution series analogous to that of test A. (The resistance refers to the tolerability of Diazinon). The compounds according to Example 1 acted in these tests against adults and larvae of *Rhipicephalus bursa* and sensitive and OP-resistant larvae of *Boophilus microplus*.

EXAMPLE 5

Acaricidal action

*Phaseolus vulgaris* (dwarf beans) have an infested piece of leaf from a mass culture of *Tetranychus urticae* placed on them 12 hours before the test for their acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25° C. The compounds according to Example 1 were active in the above test against eggs, larvae and adults of *Tetranychus urticae*.

EXAMPLE 6

Action against soil nematodes

To the test action against soil nematodes, the active substance in the concentration indicated in each case is applied to an intimately mixed with soil infected with root gall nematodes (*Meloidgyne arenaria*). Immediately afterwards, tomato cuttings are planted in the thus prepared soil in a series of tests and after a waiting time of 8 days tomato seeds are sown in another test series.

In order to assess the nematocidal action the galls present on the roots are counted 28 days after planting and sowing respectively. In this test the compounds according to Example 1 display good action against *Meloidgyne arenaria*.

EXAMPLE 7

Action against soil insects

Sterilised compost earth is homogeneously mixed with a wettable powder containing 25% of active substance so as to give concentrations of 16, 8, 4, 2, and 1 ppm. Yound zucchetti and cabbage plants were planted in the prepared soil and immediately infested with 5 *Aulacophora femoralis* larvae (age: 15 d/25° C) and 15 *Chortophila brassicae* (cabbage fly) eggs. A third corresponding soil sample is provided with slices of apple as feed and populated with 5 Pachnoda savignyi larvae (20 d/25° C). Mortality inspection is carried out 10 days after application and infestation.

The screening test with caterpillars (Agrotis Y-L$_2$) proceeds in analogous manner, except that the concentrations are 40, 20, and 10 ppm. Mallow leaves are used as feed. In the above test, the compounds according to Example 1 were active against *Aulacophora femoralis, Chortophila brassicae, Pachnoda savigny,* and Agrotis larvae.

We claim:

1. A compound of the formula

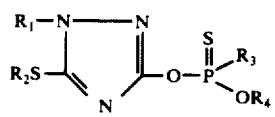

wherein
- R$_1$ represents alkyl of from 1 to 6 carbon atoms or cycloalkyl of from 3 to 6 carbon atoms,
- R$_2$ represents allyl, methallyl, 2-butenyl, 4-chloro-2-butenyl or propargyl,
- R$_3$ represents methoxy, ethoxy or ethylamino, and
- R$_4$ represents methyl or ethyl.

2. A compound of the formula

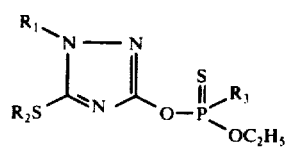

wherein R$_1$ represents methyl, ethyl, isopropyl or cyclopentyl; R$_2$ represents allyl, methallyl, 2-butenyl, 4-chloro-2-butenyl or propargyl; and R$_3$ represents ethoxy or methylamino.

3. A compound according to claim 2, of the formula

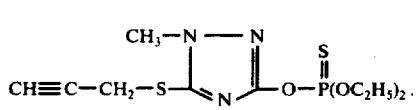

4. A compound according to claim 2, of the formula

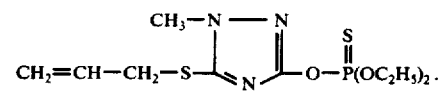

5. A compound according to claim 2, of the formula

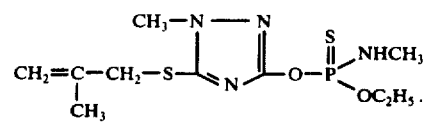

6. A compound according to claim 2, of the formula

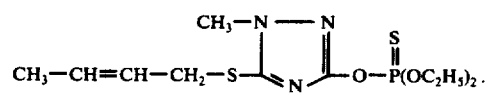

7. A compound according to claim 2, of the formula

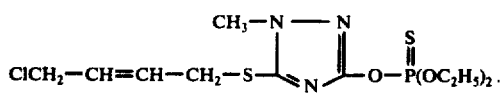

8. A compound according to claim 1, of the formula

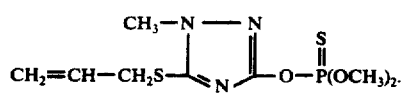

9. A compound according to claim 2, of the formula

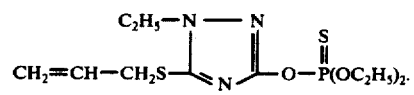

10. A compound according to claim 2, of the formula

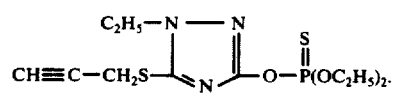

11. A compound according to claim 2, of the formula

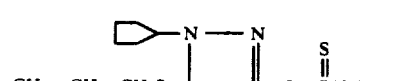

* * * * *